(12) United States Patent
Smith et al.

(10) Patent No.: US 7,723,387 B2
(45) Date of Patent: May 25, 2010

(54) SELF-NEUTRALIZING ACID PEEL FOR DERMATOLOGIC USE

(75) Inventors: Robert MacDonald Smith, Jacksonville, FL (US); Otto William Wendel, Young Harris, GA (US); Archie McBride, Pewsey (GB)

(73) Assignee: Polymer Surfaces Group, LLC, Jacksonville, FL (US)

( * ) Notice: Subject to any disclaimer, the term of this patent is extended or adjusted under 35 U.S.C. 154(b) by 671 days.

(21) Appl. No.: 11/553,149

(22) Filed: Oct. 26, 2006

(65) Prior Publication Data

US 2008/0003246 A1 Jan. 3, 2008

Related U.S. Application Data

(60) Provisional application No. 60/806,005, filed on Jun. 28, 2006.

(51) Int. Cl.
*A61K 31/19* (2006.01)
*A61K 33/00* (2006.01)
(52) U.S. Cl. .................................. 514/557; 424/722
(58) Field of Classification Search ................ None
See application file for complete search history.

(56) References Cited

U.S. PATENT DOCUMENTS

| | | | |
|---|---|---|---|
| 4,197,316 A | 4/1980 | Van Scott et al. | |
| 4,204,775 A | 5/1980 | Speer | |
| 4,316,677 A | 2/1982 | Ciavatta | |
| 4,363,815 A | 12/1982 | Yu et al. | |
| 4,704,278 A * | 11/1987 | Wu et al. | 424/688 |
| 4,774,057 A | 9/1988 | Uffenheimer et al. | |
| 5,091,171 A | 2/1992 | Yu et al. | |
| 5,422,370 A | 6/1995 | Yu et al. | |
| 5,425,938 A | 6/1995 | Znaiden et al. | |
| 5,595,984 A | 1/1997 | Blank | |
| 5,615,801 A | 4/1997 | Schroeder et al. | |
| 5,648,395 A | 7/1997 | Yu et al. | |
| 5,665,776 A | 9/1997 | Yu et al. | |
| 5,677,340 A | 10/1997 | Yu et al. | |
| 5,681,853 A | 10/1997 | Yu et al. | |
| 5,702,688 A | 12/1997 | Yu et al. | |
| 5,735,436 A | 4/1998 | Schroeder et al. | |
| 5,819,988 A * | 10/1998 | Sawhney et al. | 222/137 |
| 5,827,882 A | 10/1998 | Yu et al. | |
| 5,877,212 A | 3/1999 | Yu et al. | |
| 5,883,085 A | 3/1999 | Blank et al. | |
| 5,886,042 A | 3/1999 | Yu et al. | |
| 5,922,764 A | 7/1999 | Cantin et al. | |
| 5,958,436 A | 9/1999 | Hahn et al. | |
| 6,455,076 B1 | 9/2002 | Hahn et al. | |
| 6,471,972 B1 | 10/2002 | Bonte | |
| 6,756,069 B2 | 6/2004 | Scoville et al. | |
| 2004/0048836 A1 * | 3/2004 | Wilmott | 514/159 |

FOREIGN PATENT DOCUMENTS

| | | |
|---|---|---|
| FR | 2 720 643 | 12/1995 |
| GB | 2 328 374 | 2/1999 |

OTHER PUBLICATIONS

Bennett and Henderson, 2003. introduction to cosmetic dermatology. Current Problems in Dermatology, vol. 15(2): 43-83.*
Moy et al, 2002. Glycolic Acid Peels. Bioavailable Alpha Hydroxy Acid. pp. 21-24.*
Hans Udo Kraechter, "Amphoteric Hydroxy Complexes: AHAs with Reduced Stinging and Irritation," Cosmetics & Toiletries magazine, Jan. 2001, vol. 116, No. 1, p. 47-51.
Ruey J. Yu, "A Discussion of Control-Release Formulations of AHAs," Costmetic Dermatology, Oct. 2001, pp. 15-18.
Meyer Rosen, "Delivery System Handbook for Personal Care and Cosmetic Products: Technology, Applications, and Formulations," 2005, William Andrew Publishing, Inc., pp. 881-908.
F.A. Anderson, Final Report on the Safety Assessment of Glycolic Acid, Ammonium, Calcium, Potassium, and Sodium Glycolates, Methyl, Ethyl, Propyl, and Butyl Glycolates, and Lactic Acid, Ammonium, Calcium, Potassium, Sodium, and Tea-Lactates, Methyl, Ethyl, Isopropyl, and Butyl Lactates, and Lauryl, Myristyl, and Cetyl Lactates; International Journal of Toxicology, vol. 17 (Suppl 1); 1998; 3 pages.

* cited by examiner

*Primary Examiner*—Jean C Witz
*Assistant Examiner*—Raymond P Yeager
(74) *Attorney, Agent, or Firm*—Pedigo Law Firm, PLLC

(57) ABSTRACT

A dermatologic peel comprising alpha hydroxyl acid and metal hydroxide nanocomplexes as neutralizing agents to continually reduce the activity of the system when the acid and neutralizer components are mixed. For example, a 30% glycolic acid gel mixed with a fluidized magaldrate neutralizer can be applied to the skin and will self-neutralize to a skin-compatible pH within a few minutes, effectively exfoliating the skin without a separate neutralization step. The peel is advantageously applied from a two-component system that mixes the components.

15 Claims, 7 Drawing Sheets

SELF-NEUTRALIZING ACID PEEL FOR DERMATOLOGIC USE

BACKGROUND OF THE INVENTION

This invention relates to dermatologic chemical peels prepared from alpha hydroxy acids ("AHAs"). Chemical peels have been used for centuries to improve personal appearance and rejuvenate the skin. Chemical peels exfoliate the skin to remove dead skin cells from the surface of the skin and to expose fresh skin cells, facilitating new growth and a more youthful look. One of the earlier such peels was created from sour milk, which contains the AHA lactic acid. Modern chemical peels typically use glycolic acid, or to a lesser extent, lactic acid, as the primary active AHA. The skin care industry documents significant improvement in characteristics associated with acne, age spots, wrinkles, photo-damage and other age-related skin changes, and numerous other skin conditions. AHAs support a world-wide multi-billion dollar anti-aging skin products industry.

Established industry practice has typically been to provide dermatologic peels in two broad categories, professional strength and consumer products. Professional strength peels include a higher concentration of acid than over-the-counter consumer retail products, are designed for occasional use, and normally are administered in controlled conditions by an individual trained to do so. For example, a professional strength face peel may be applied by a therapist at a resort health spa or in a salon setting or physician's office. A typical professional glycolic acid peel treatment is applied at an acid concentration of from about 20% to 35% by weight at a pH of approximately 3.0 for a period of about three to five minutes. The therapist then deactivates the peel with a buffer solution, typically sodium bicarbonate, which neutralizes the acid, or rinses the skin liberally with water to remove the acid and to bring the acid condition of the skin to a pH level similar to normal skin. The therapist usually monitors individual perceptions of redness, stinging, or pain and blistering and can end the treatment, if necessary, based on these perceptions.

On the other hand, consumer products intended for home use or other uncontrolled settings normally include a concentration of acid sufficiently low to reduce the possibility of negative effects, even if the consumer uses the peel frequently or does not rinse it off. Thus, consumer products may compromise efficacy for a degree of control inherent in application of a low acid formulation sufficient to preclude overexposure. A typical consumer grade glycolic acid peel contains acid at a concentration of about 10% or less and is applied at a pH of 3.5 or more. Although the pH is acid, the concentration of acid in solution is dilute to reduce the chance of redness, stinging or blistering, even if the consumer does not rinse.

It would be desirable to improve acid peels and to provide acid peels that can achieve better or at least equivalent results than those now available and with less intervention required, while at the same time avoiding the likelihood of redness, stinging, burning, or blistering caused by excessive exposure to the low pH of professional strength peel formulations.

SUMMARY OF THE INVENTION

This invention relates to a two-component system for delivering a self-neutralizing alpha hydroxy acid composition for dermatologic applications. The system can deliver an initial relatively high acid concentration that can then approximate a pH compatible with most skin types within a desired, predetermined, dermatologically appropriate time period. The acid composition of the invention requires no separate neutralization step at concentrations normally considered professional strength. The composition can be formulated at a variety of acid concentrations and pH levels for different needs, including different skin types and sensitivities. The invention includes, in addition to the delivery system and the acid composition, the method of making and applying the composition.

The two-component system of the invention includes a dual-component syringe having a pair of dispensing tubes, one tube of which contains the acid component and the other of which contains the neutralizer component. The tubes are fitted with pistons at one end thereof for dispensing the components and at the other end with a static mixing head in a chamber that is in flow communication with each tube. The pistons eject the components into the common chamber for intimate contact in the static mixing head and then through a small aperture at the distal end of the mixing chamber for application. Alternatively, a user can mix the components at the time of application using any suitable mixing device.

The acid component will typically be an AHA, usually glycolic acid, although it should be recognized that any of the AHAs is contemplated. Glycolic acid typically is preferred. Premixed formulations of acid and neutralizer currently available on the market can be used as the acid component in the two-component system of the invention, although not necessarily with equivalent results. These premixed formulations are normally at a shelf-stable pH and are not self-neutralizing. When further mixed with the neutralizer component in the two-component system of the invention, the premixed acid formulations should be capable of providing a managed, continual increase in pH characteristic of the self-neutralizing dermatologic peel of the invention. Provided the premixed acid formulations are not overly diluted in the first place, the benefits of the invention can still be realized even though the acid concentration is further diluted with neutralizer in the practice of the invention.

A number of acid neutralizer components are believed to be suitable for use as fluidized neutralizer components for neutralizing an acid component in connection with the two-component system of the invention. Magaldrate is suited for use in the practice of the invention. Magaldrate is a mixture of aluminum hydroxide and magnesium hydroxide nanoparticles co-precipitated from aluminum chloride and magnesium sulfate. The sulfate is believed to enable fluidization of a higher density of metal hydroxide. Having a greater concentration of metal hydroxide nanoparticles in a fluid state increases the strength of the neutralizer. Aluminum hydroxide and magnesium hydroxide separately or co-blended are believed to be useful as fluidized gels, although not necessarily with results equivalent to magaldrate. Other metal hydroxides may also be substituted for magaldrate, although it should be recognized that although a metal hydroxide may function well to neutralize acid, not all metal hydroxides are suitable for use in dermatologic applications. Inorganic and organic amphoteric compounds sometimes used to dilute acids for dermatologic applications may be useful in the practice of the invention, although it should be recognized that in the practice of the invention, these compounds are mixed with the acid as a neutralizer component of a two-component system and immediately applied to the skin.

For example, in one embodiment, a fluidized magaldrate composition can be formulated as a neutralizer with glycolic acid in a professional strength acid composition using the two-component system of the invention. The system separates the magaldrate and acid components and then intimately mixes the components at the time of application. This composition provides a high initial concentration of acid at a pH sufficiently low to achieve efficacious results as a dermatologic peel. The magaldrate component neutralizes the acid continually over a predetermined period of time while increasing the pH and reducing the activity of the peel to the point that no separate or additional neutralization step is required to terminate treatment. Although not wishing to be bound by theory, it is believed that the AHA acid component forms a nanogel complex with the intimately mixed magaldrate neutralizer that increases the activity of the acid while simultaneously slowing down neutralization to a controlled, reproducible and continual rate.

When using the two component system of the invention, the acid and neutralizer components typically will be mixed 50/50 by volume for convenience at the time of application. While perhaps somewhat less practical, other volume percentages could be used. If the acid and neutralizer compositions are adjusted accordingly, then the mixed system should be of the same acid concentration and neutralize at a similar rate as a 50/50 volume split. Generally speaking, the tubes of the dual syringe are of the same volume and dispense the same volume of material simultaneously into the common static mixing chamber. Thus, the acid component is normally diluted by half-volume in application, which roughly correlates to half the weight percentage of acid as compared to the unmixed acid component. Other ratios of the two components can be used, if desired, for different neutralization profiles and endpoints.

Acid component concentrations ranging from 10% to 70% acid by weight are contemplated, although concentrations of from 20% to 50% should be somewhat more typical, and from 30% to 50% should be common. For example, glycolic acid can be formulated at a 30% acid concentration and at a pH of from 1.8 to 2.2 for the acid component, which will result in a nominal 15% acid concentration in a freshly mixed dermatologic composition that dilutes the acid component by half. Once mixed and blended, the composition begins continually to increase in pH and so, in the case of dermatologic peel use, a user or technician applies the composition to the skin immediately upon completing mixing, typically from the dispensing nozzle on the static mixer of a dual-component syringe. It should be recognized that the components could be mixed in any suitable fashion. Compatible skin pH is reached as the composition neutralizes over time, normally within 3 to less than 10 minutes, depending on the initial acid concentration and pH of the mixed components. A rinse may follow treatment, but the treatment requires no separate neutralization.

Thus, the invention provides, among other things, a two-component system for supplying a new self-neutralizing dermatologic peel composition that neutralizes over time when applied to the skin, requiring no separate neutralization or removal steps to stop the action of the acid on the skin, even at higher strengths normally applied by trained technicians.

BRIEF DESCRIPTION OF THE DRAWINGS

Having described the invention in general terms, reference will now be made to the accompanying drawings, wherein.

DETAILED DESCRIPTION OF THE INVENTION

Figure 1:
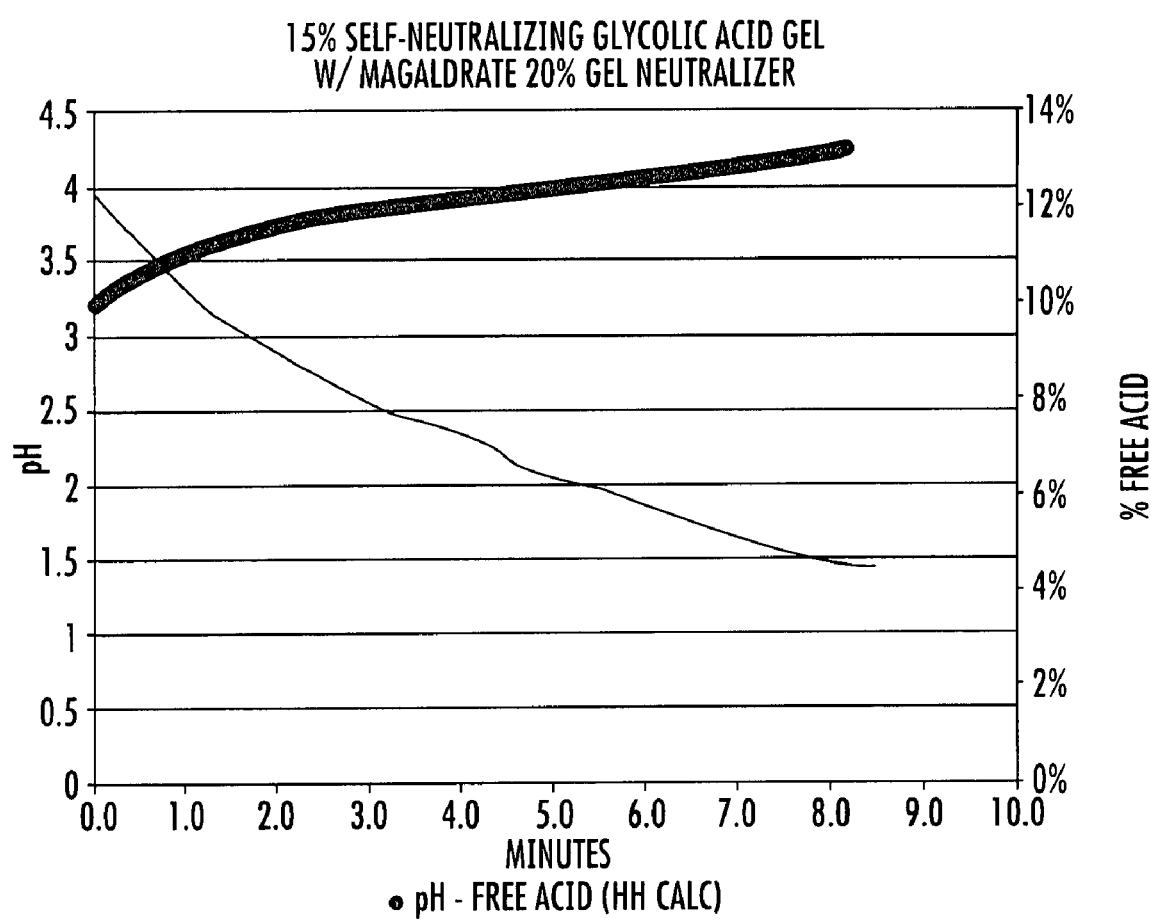
FIG. 1 is a graphical representation of pH on the left hand ordinate and percent free acid on the right hand ordinate plotted against time on the abscissa and shows for a 15% self-neutralizing glycolic acid gel, which has been prepared from a nominal 30% glycolic acid gel and a 20% magaldrate gel neutralizer mixed 50/50 by volume, that as pH continually increases over a period of time, the free acid available for reaction decreases at a similar rate.

The invention will now be described more fully hereinafter with reference to the accompanying drawings, in which some, but not all concepts of the invention are shown. Indeed, the invention may be embodied in many different forms and should not be construed as limited to the examples set forth herein; rather, the embodiments provided in this disclosure are intended to satisfy applicable legal requirements.

In formulating alpha hydroxy acid (AHA) peel compositions, it is desirable to use the smallest amount of acid needed to accomplish the desired exfoliation over a defined and predetermined treatment time. Generally, the least amount of AHA necessary to promote efficacious exfoliation is sometimes referred to in the industry as the "bioavailable concentration" ('BAC'). Performance of alpha hydroxy acid-based skin care products can be correlated with the quantity of bioavailable acid, which is that acid that is available to react with the skin and not bound up in a form that precludes useful work of exfoliation. In a given acid peel concentration, not all of the acid is available to do useful work.

Bioavailable acid can be correlated with free acid, which is based upon the pH of the acid solution and the concentration of the acid in solution. Table 1, below, provides BAC data for various concentrations of the AHA glycolic acid at ambient conditions for specific pHs. It is assumed that the BAC is equivalent to the free acid concentration, which is the total concentration of acid minus the amount of acid in a glycolate salt complex, calculated as a weight percent. The relationship between free acid and pH follows the Henderson-Hasselbalch equation:

$$pH = pKa + \log([A^-]/[HA])$$

where [HA] is the concentration of the free acid, [A$^-$] is the concentration of acid in the glycolate salt, and pKa is the disassociation constant of glycolic acid.

TABLE 1

Bioavailability of Glycolic Acid as a Function of pH

| pH | Bioav. @25° C. | Bioavailable Concentration (wt %) at Glycolic Acid Concentration | | | | | | |
|---|---|---|---|---|---|---|---|---|
| | | 4 | 8 | 12 | 20 | 35 | 50 | 70 |
| 2.00 | 0.99 | 4 | 8 | 12 | 20 | 35 | 50 | 69 |
| 2.50 | 0.96 | 3.8 | 7.7 | 12 | 19 | 34 | 48 | 67 |
| 3.00 | 0.87 | 3.5 | 7 | 10 | 17 | 30 | 44 | 61 |
| 3.20 | 0.81 | 3.2 | 6.5 | 9.7 | 16 | 28 | 41 | 57 |
| 3.40 | 0.73 | 2.9 | 5.8 | 8.8 | 15 | 26 | 37 | 51 |
| 3.60 | 0.63 | 2.5 | 5 | 7.6 | 13 | 22 | 32 | 44 |
| 3.80 | 0.52 | 2.1 | 4.2 | 6.2 | 10 | 18 | 26 | 36 |
| 3.83 | 0.5 | 2 | 4 | 6 | 10 | 17.5 | 25 | 35 |
| 4.00 | 0.4 | 1.6 | 3.2 | 4.8 | 8 | 14 | 20 | 28 |
| 4.20 | 0.3 | 1.2 | 2.4 | 3.6 | 6 | 11 | 15 | 21 |
| 4.40 | 0.21 | 0.8 | 1.7 | 2.5 | 4.2 | 7.4 | 11 | 15 |
| 4.60 | 0.15 | 0.6 | 1.2 | 1.8 | 3 | 5.3 | 7.5 | 11 |
| 4.80 | 0.1 | 0.4 | 0.8 | 1.2 | 2 | 3.5 | 5 | 7 |
| 5.00 | 0.06 | 0.2 | 0.5 | 0.7 | 1.2 | 2.1 | 3 | 4.2 |

It should be noted that BAC as calculated is independent of time and is calculated based on an acid concentration at any given moment in time. The above values for BAC reported in Table 1 generally are reflective of the initial values for a glycolic acid as it is applied to the skin, whether as a premix designed to be neutralized in the conventional manner at the end of the peel or in the two-component self-neutralizing composition of the invention. In the practice of the invention, it should be recognized that the BAC continually reduces over time until the treatment is ended. The pH of the gel continually increases until it reaches a point compatible with human skin. This is in contrast to a conventional dermatologic treatment, in which the BAC and the pH are assumed to remain constant over the treatment time. Consequently, in conventional practice, treatment time is generally selected as that time that provides the desired therapeutic benefit for a given constant BAC of acid and is generally determined empirically. When the conventional treatment time is ended, the therapist neutralizes or rinses the acid to drive the BAC to zero. In contrast, in the practice of the invention, the initial BAC continually reduces over time rather than being considered to remain constant until neutralization.

At the beginning of the treatment in accordance with the invention, a high percentage of acid in the formulation is bioavailable as free acid that penetrates and begins the exfoliation process at the BAC calculated for that free acid concentration. The formulation of the invention includes acid neutralizing agents that begin immediately to neutralize the acid when the components are mixed. While not wishing to be bound by theory, it is believed that the neutralizer may form a nanogel complex that slows the rate of neutralization. Particularly in the case of magaldrate, the presence of sulfate ion is believed to allow a higher density of the metal hydroxide nanoparticles to be fluidized, which increases the speed of neutralization, and which is moderated by the interaction of the acid and neutralizer. Whatever the reasons, the overall impact is that the BAC decreases at a rate useful for a self-neutralizing exfoliation.

As previously stated, a number of acid neutralizing compounds are known that should be useful in the practice of the invention. One suitable such neutralizer is magaldrate. A fluidized magaldrate is described in Wu et al. U.S. Pat. No. 4,704,278. Magaldrate is described as a combination of from at least about 18% by weight to not more than 26% by weight aluminum hydroxide and from at least about 29% by weight to not more than 40% by weight magnesium hydroxide that is sometimes called aluminum magnesium hydroxidesulfate. Other neutralizers include hydrated, insoluble inorganic salts of calcium, aluminum, magnesium, sodium, and bismuth.

Yu et al. U.S. Pat. No. 5,091,171 discloses a number of acid neutralizers that should be useful in the practice of the invention, including organic and inorganic amphoteric compounds and organic pseudoamphoteric compounds. Inorganic oxides include certain metallic oxides including aluminum oxide, zinc oxide and others. The compounds disclosed in the Yu et al. patent for use in connection with AHAs as premixes should be useful in the practice of the invention. It should be recognized that the invention employs neutralizers as separate components not mixed with the acid component until application, and that the acid component may have included the neutralizer components prior to further mixing at application. Yu U.S. Pat. No. 5,702,688 describes a premixed formulation of glycolic acid and a neutralizer believed to be useful as the acid component in connection with the two-component system of the invention. The contents of Yu et al. U.S. Pat. Nos. 5,091,171 and 5,702,688 are incorporated herein by reference in their entirety.

Any of the alpha hydroxy acids are contemplated for use in the practice of the invention, although not necessarily with equivalent results. Glycolic acid is typically used in peels and the examples illustrated below all use glycolic acid. Other AHAs contemplated for use in connection with the invention include lactic acid; ammonium, calcium, potassium, and sodium glycolates; methyl, ethyl, propyl, and butyl glycolates; ammonium, calcium, potassium, sodium, and TEA-lactates; methyl, ethyl, isopropyl, and butyl lactates; and lauryl, myristyl, and cetyl lactates.

For convenience, the neutralizer and acid components of the invention typically are applied 50/50 by volume, which enables determination of the initial acid concentration, pH and thus BAC or free acid, to be readily determined and controllable and also provides for ease of packaging and dispensing the two components. Of course, it should be recognized that the initial 50/50 volume blend can be varied as desired to achieve similar initial acid concentrations in the self-neutralizing composition of the invention.

The two-component system of the invention can be dispensed through a variety of designs and there are a number of dual compartment systems believed to be suitable for simultaneously mixing and dispensing the acid and neutralizer components. A dual compartment syringe with a static mixing head is particularly suitable and can be preloaded and packaged for single use. Dual compartment syringes normally include a pair of dispensing tubes into which the components are loaded, each tube being fitted at one end with a piston for uniformly discharging the component. A common chamber containing a static mixer receives the components, which are mixed by travel along the flights of the mixer, the intimately mixed components exiting the common mixing chamber at a tapered end thereof opposite the dispensing tubes. It should be recognized that the dual compartment system can be packaged in a variety of ways to achieve the same objective of dispensing freshly and intimately mixed acid and neutralizer components for dermatologic use. Of course, the user or technician can simply mix the components in any suitable receptacle and apply them, if desired.

EXAMPLES

The following examples are provided to illustrate the invention, and should be considered in support of, and not in limitation of, the full scope of the invention, which is defined by the claims.

Example 1

As shown in Example 1 and those following, an acid component is mixed with a neutralizer component. The acid and neutralizer are both supplied as gels, and the composition of each component is listed.

| Acid Gel Component 30% Glycolic Acid Gel | Grams | Percent | Effective Acid |
|---|---|---|---|
| D.I. Water | 46.14 | 46.1% | |
| Cellosize PCG-10 | 0.8 | 0.8% | |
| Ticazan (Salt resistant) | 0.2 | 0.2% | |
| Propylene glycol | 10 | 10.0% | |
| Glycolic Acid, 70% | 42.86 | 42.9% | 30.0% |
| | 100 | 100% | |

| Neutralizer Gel Component Magaldrate Gel 20% | |
|---|---|
| Aluminum Hydroxide | 12% |
| Magnesium Hydroxide | 8% |
| Sulfate | <1.5% |

Starting from a 70% glycolic acid solution, a nominal 30% glycolic acid gel was prepared by mixing the acid with de-ionized water, Cellosize PCG-10, a salt-resistant Ticaxan, and propylene glycol in the weight percentages shown. Cellosize Polymer PCG-10 is a Dow Chemical Company product, described [at www.cellosize.com] on the world wide website for Cellosize under the domain name cellosize.com as a hydroxyethyl cellulose nonionic water soluble polymer for use as a thickening agent and emulsion stabilizer in the personal care market for cosmetic and toiletry formulations. Ticaxan is a product of TIC Gums, Belcamp, Md., and is a xanthan gum sold as a salt tolerant powder and described [at www.ticgums.com] on the world wide website for TIC Gums under the domain name ticgums.com. Hydroxyethyl cellulose and xanthan gum function together in a synergistic fashion to enable ready adjustment of viscosity at relatively lower concentrations than would be required if either was used alone. Propylene glycol is believed to enhance penetration of alpha hydroxy acids by modifying the permeability of the stratum corneum. A small, but effective amount of an antibacterial agent was added to the formulation and did not impact performance.

Ten grams of the nominal 30% acid gel were mixed with 10 grams of a neutralizer magaldrate gel in a 50 ml beaker, which approximated the 50/50 volume split of a dual syringe delivery system. The magaldrate was a fluidized gel that contained a nominal 20% concentration of magaldrate. Magaldrate 20% fluid gel is available from SPI Pharma located in Wilmington, Del. Free acid in the self-neutralizing acid formulation of the invention is a nominal 15.0% by weight, the acid concentration having been reduced by half by mixing the 30% glycolic acid gel with the magaldrate gel in a 50/50 weight ratio.

The pH of the gel mixture was measured over time using a pH data acquisition system. FIG. 1 shows a graph of the pH of the system of Example 1 as neutralization occurs over time. The free acid equilibrium concentration was calculated from the pH of the system over time based on the Henderson-Hasselbalch equation. The free acid, in percent by weight of the mixed solution starting from a nominal 15% by weight self-neutralizing glycolic acid solution, is also shown over time on the graph in FIG. 1 and is correlated with pH.

As illustrated in FIG. 1, as the pH of the system increases continually over time, the percent free acid continually reduces, dropping off quickly at first. Free acid decreases almost immediately upon mixing. The first probe measurement of the pH is about 3.2 and reflects a free acid concentration of about 12.5%. Within about 9 minutes or less, the system has reached a pH of about 4.3, which approximates the pH of the acid mantel of the stratum corneum ("SC"), and therefore is within the normal pH gradient of the SC for most skin types. The amount of bioavailable acid ("BAC") in the system has been reduced to the point that exfoliation as the result of the chemical peel has virtually ceased.

Example 2

| Acid Gel Component 30% AHCare G-60 Gel | Grams | Percent | Effective Acid |
|---|---|---|---|
| D.I. Water | 45.8 | 45.8% | |
| Cellosize PCG-10 | 0.9 | 0.9% | |
| Ticaxan (Salt resistant) | 0.3 | 0.3% | |
| Propylene Glycol | 5 | 5.0% | |
| AHCare G-60 | 48 | 48.0% | 30.0% |
| | 100.0 | 100% | |

| Neutralizer Gel Component Magaldrate Gel 20% | |
|---|---|
| Aluminum Hydroxide | 12% |
| Magnesium Hydroxide | 8% |
| Sulfate | <1.5% |

Example 2 is prepared similarly to Example 1. In Example 2, a nominal 30% glycolic acid gel component is prepared from AHCare G-60 acid solution rather than the 70% glycolic acid of Example 1. AHCare G-60 is a premixed glycolic acid and neutralizer gel at 62.5% glycolic acid by weight that is believed to be described in Yu U.S. Pat. No. 5,091,171. The product is available through Laboratoires Serobiologiques, a Division of Cognis France. Somewhat less propylene glycol was required, 5.0% by weight as compared to 10.0% by weight with the 70% glycolic acid of Example 1, but approximately the same amounts of de-ionized water, Cellosize PCG-10, and Ticaxan were used.

Ten grams of the acid gel at 30% acid by weight and 10 grams of the neutralizer magaldrate gel were mixed together in a 50 ml beaker and the pH of the gel mixture was measured over time using a pH data acquisition system. The same 20% by weight magaldrate gel as was used in Example 1 was used in connection with the formulation of Example 2. Free acid in the self-neutralizing acid formulation of the invention is a nominal 15.0% by weight, the acid concentration having been reduced by half by mixing the 30% AHCare G-60 gel with the magaldrate gel in a 50/50 weight ratio.

Figure 2:
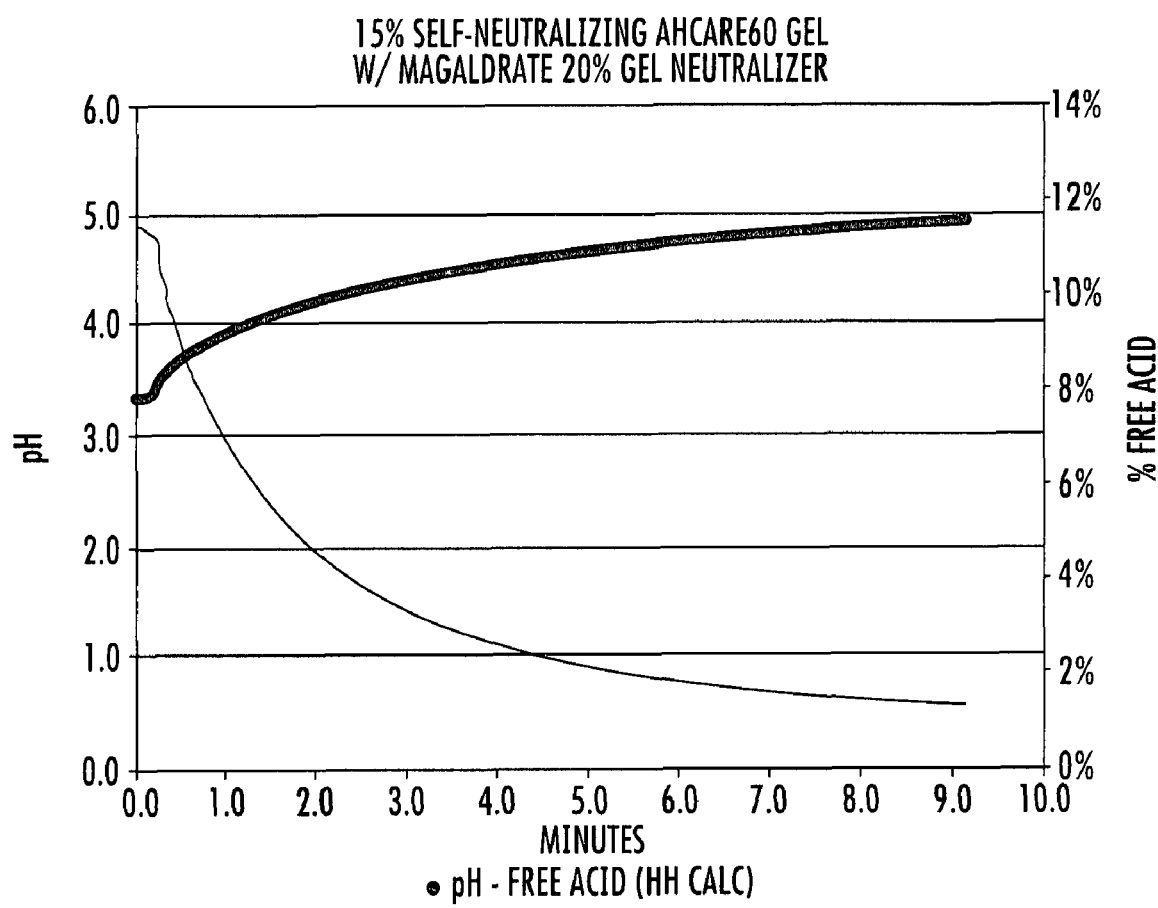
FIG. 2 is a graph similar to FIG. 1, showing a 15% self-neutralizing alpha hydroxy acid concentration of the invention prepared from 20% magaldrate gel neutralizer and a premixed acid and neutralizer formulation (30% acid equivalent) after further mixing in the two-component system of the invention.

The pH of the gel mixture was measured over time using a pH data acquisition system. FIG. 2 shows a graph of the pH of the system of Example 2 as neutralization occurs over time. The free acid equilibrium concentration was calculated from the pH of the system over time based on the Henderson-Hasselbalch equation. The free acid, in percent by weight of the mixed solution starting from a nominal 15% by weight self-neutralizing AHCare G-60 gel, is also shown over time on the graph in FIG. 2 and is correlated with pH.

As illustrated in FIG. 2, as the pH of the system increases continuously over time, from an initial pH of about 3.3 to a final pH of about 4.9, the percent free acid also continuously reduces from an initial approximately 11.5% to a final approximately 1%. Within about 4 minutes or less, the system has reached a pH of about 4.5, approximating the pH of the SC acid mantel, and therefore is within the normal pH gradient of the SC for most skin types. The BAC has been reduced to the point that exfoliation as the result of the chemical peel has virtually ceased.

Example 3

| Acid Gel Component 40% Glycolic Acid Gel | Grams | Percent | Effective Acid |
|---|---|---|---|
| D.I. Water | 31.9 | 31.9% | |
| Cellosize PCG-10 | 0.8 | 0.8% | |
| Ticaxan (Salt resistant) | 0.2 | 0.2% | |
| Propylene glycol | 10 | 10.0% | |
| Glycolic Acid, 70% | 57.1 | 57.1% | 40.0% |
| | 100 | 100% | |

| Neutralizer Gel Component Magaldrate Gel 20% | |
|---|---|
| Aluminum Hydroxide | 12% |
| Magnesium Hydroxide | 8% |
| Hydroxide Sulfate | <1.5% |

The self-neutralizing gel of Example 3 was prepared similarly to that of Examples 1 and 2, starting from a 70% glycolic acid solution to produce a nominal 40% glycolic acid gel component. The actual free acid was determined to be 40% by weight. The same 20% magaldrate gel was used as was used in the previous examples. Ten grams of the acid gel and 10 grams of the neutralizer magaldrate gel were mixed together in a 50 ml beaker and the pH of the gel mixture was measured over time using a pH data acquisition system. Free acid of the mixture was a nominal 20% by weight, the acid concentration having been reduced by half by mixing the 40% glycolic acid gel with the magaldrate gel in a 50/50 weight ratio.

Figure 3:
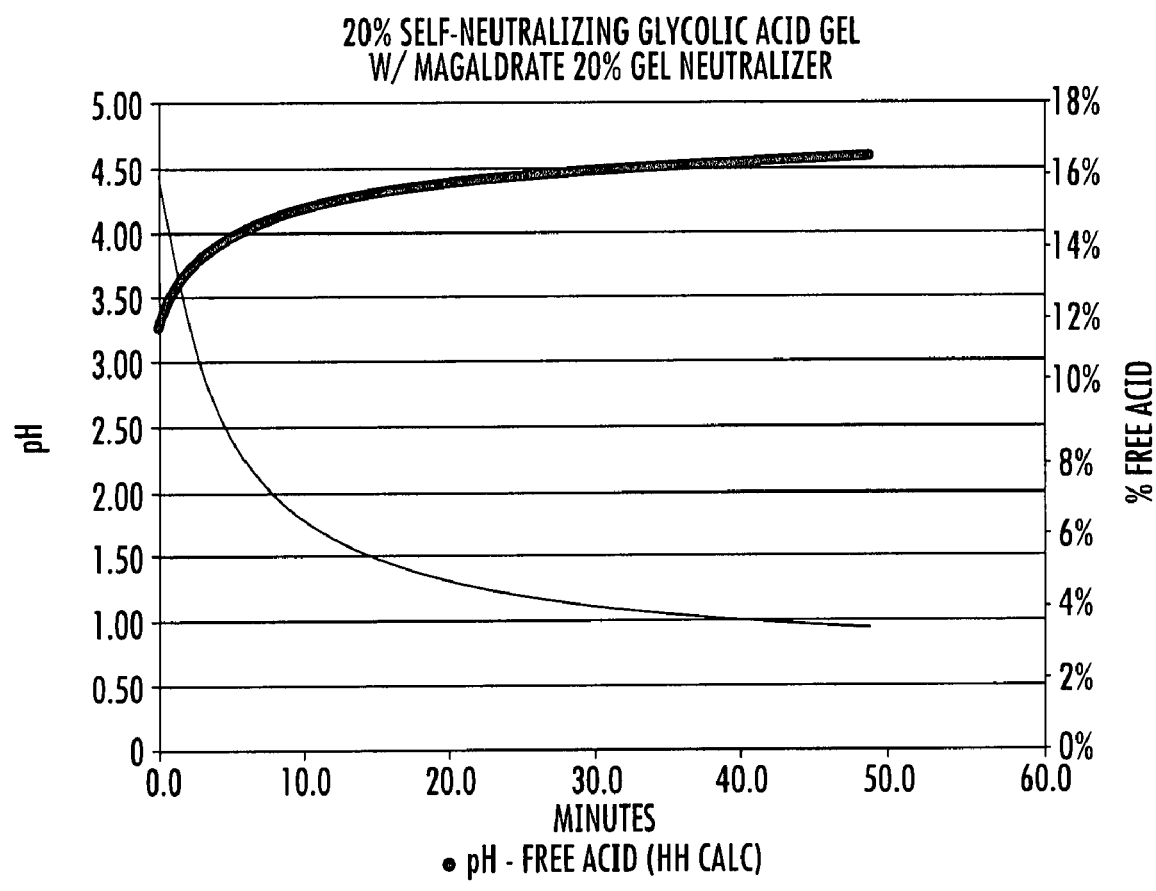
FIG. 3 is a graph similar to FIG. 1, showing a 20% self-neutralizing glycolic acid gel.

FIG. 3 shows a graph of the pH of the system of Example 3 as neutralization occurs over time. The free acid, in percent by weight of the mixed solution starting from a nominal 20% by weight glycolic acid solution, is also shown correlated with pH and is calculated from the pH as was done in the previous examples. As illustrated in FIG. 3, the pH of the system increases continually over time, starting from about 3.3 and increasing continually to about 4.5. The percent free acid continuously reduces from about 16% to less than 4% within about 50 minutes. Within about 4 minutes, the system has reached a pH of about 4.5, approximating the pH of the SC acid mantel, and therefore is within the normal pH gradient of the SC for most skin types. The BAC in the system has been reduced to the point that exfoliation as the result of the chemical peel has virtually ceased.

Example 4

| Acid Gel Component 50% AHCare G-60 Gel | Grams | Percent | Effective Acid |
|---|---|---|---|
| D.I. Water | 13.8 | 13.8% | |
| Cellosize PCG-10 | 0.9 | 0.9% | |
| Ticaxan (Salt resistant) | 0.3 | 0.3% | |
| Propylene Glycol | 5 | 5.0% | |
| AHCare G-60 | 80 | 80.0% | 50.0% |
| | 100 | 100% | |

| Neutralizer Gel Component Magaldrate Gel 20% | |
|---|---|
| Aluminum Hydroxide | 12% |
| Magnesium Hydroxide | 8% |
| Sulfate | <1.5% |

The self-neutralizing gel of Example 4 was prepared with an acid gel component from a 62.5% solution of glycolic acid as AHCare G-60 mixed with de-ionized water, Cellosize PCG-10, Ticaxan, and propylene glycol. The acid gel component had an actual free acid content of 50.0% by weight. The same 20% magaldrate gel was used as was used in the previous examples. Ten grams of the acid gel and 10 grams of the neutralizer magaldrate gel were mixed together in a 50 ml beaker and the pH of the gel mixture was measured over time using a pH data acquisition system. Free acid of the mixture was a nominal 15% by weight, the acid concentration having been reduced by half by mixing the 20% glycolic acid gel with the magaldrate gel in a 50/50 weight ratio.

Figure 4:
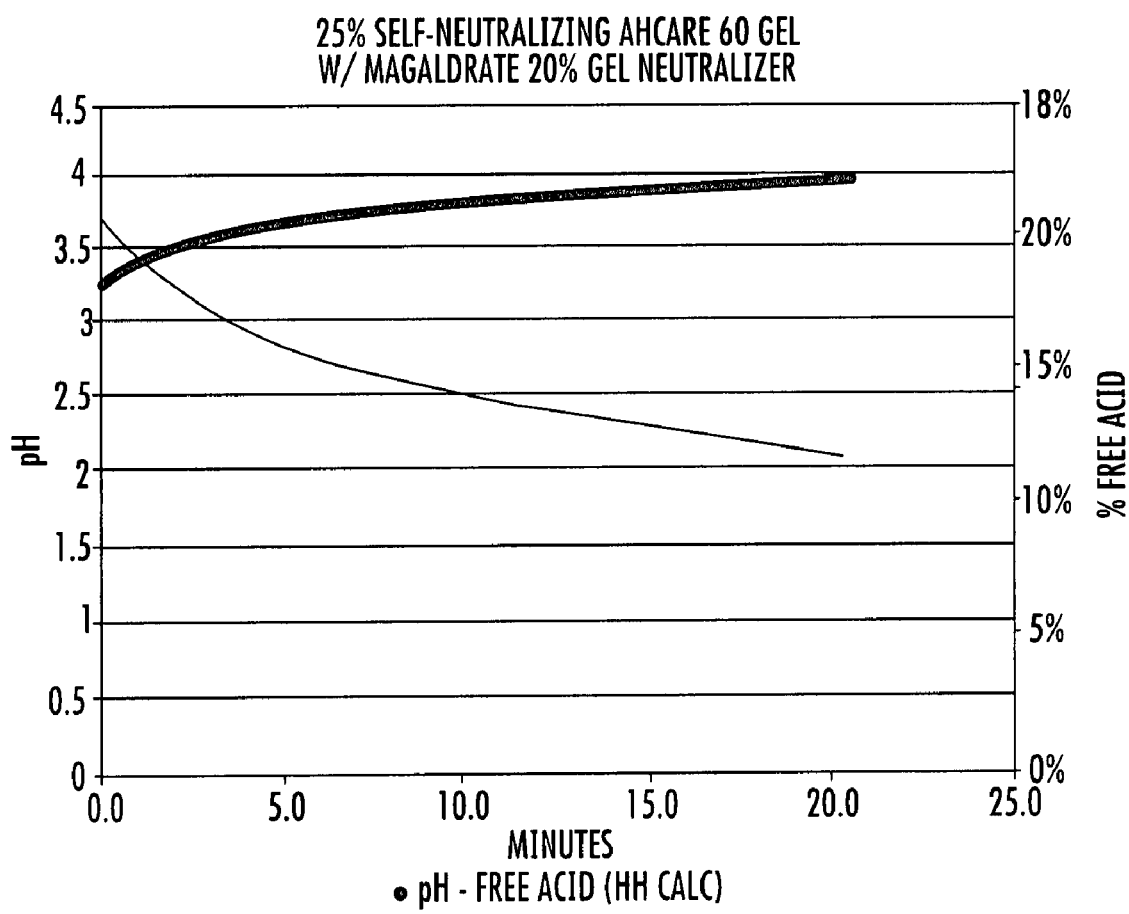
FIG. 4 is a graph similar to FIG. 1, showing a 25% self-neutralizing alpha hydroxy acid concentration of the invention prepared from a 20% magaldrate gel neutralizer and a premixed acid and neutralizer formulation (50% acid) after further mixing in the two-component system of the invention.

FIG. 4 shows a graph of the pH of the system of Example 4 as neutralization occurs over time. The free acid, in percent by weight of the mixed solution starting from a nominal 25% by weight AHCare G-60 acid solution, is also shown correlated with pH. The free acid equilibrium concentration is calculated from the Henderson-Hasselbalch equation based on the pH of the system over time. As illustrated in FIG. 4, the pH of the system increases continually over time, from an initial pH of about 3.3 to a final pH of about 4.0. The percent free acid continually reduces from an initial approximately 20% to a final approximately 12% within about 20 minutes. Within about 20 minutes or less, the system has reached a pH approximating the SC acid mantel, and therefore is within the normal pH gradient of the SC for most skin types. The BAC in the system has been reduced to the point that exfoliation as the result of the chemical peel has virtually ceased.

Example 5

| Acid Gel Component 30% Glycolic Acid Gel | Grams | Percent | Effective Acid |
|---|---|---|---|
| D.I. Water | 46.14 | 46.1% | |
| Cellosize PCG-10 | 0.8 | 0.8% | |
| Ticaxan (Salt resistant) | 0.2 | 0.2% | |

-continued

| Acid Gel Component 30% Glycolic Acid Gel | Grams | Percent | Effective Acid |
|---|---|---|---|
| Propylene glycol | 10 | 10.0% | |
| Glycolic Acid, 70% | 42.86 | 42.9% | 30.0% |
| | 100 | 100% | |

| Neutralizer Gel Component Co-Blend of Aluminum Hydroxide and Magnesium Hydroxide | |
|---|---|
| Aluminum Hydroxide | 12% |
| Magnesium Hydroxide | 8% |
| Carbonate | Present |

The same 30% glycolic acid gel is used in Example 5 as was used in Example 1. However, instead of using the 20% magaldrate neutralizer of Example 1 to blend with the acid component, Example 5 employs a co-blend of aluminum hydroxide and magnesium hydroxide present in similar amounts as the magaldrate co-precipitated product. Carbonate is present in small amounts as noted on the above table. Carbonate is believed to act similarly to sulfate in magaldrate and to increase the activity of the dermatologic action while moderating neutralization.

Ten grams of the acid gel and 10 grams of the neutralizer co-blended aluminum hydroxide and magnesium hydroxide gel were mixed together in a 50 ml beaker and the pH of the gel mixture was measured over time using a pH data acquisition system. Free acid was determined to be a nominal 15.0% by weight, the acid concentration having been reduced by half by mixing the acid gel with the neutralizer gel in a 50/50 weight ratio.

Figure 5:
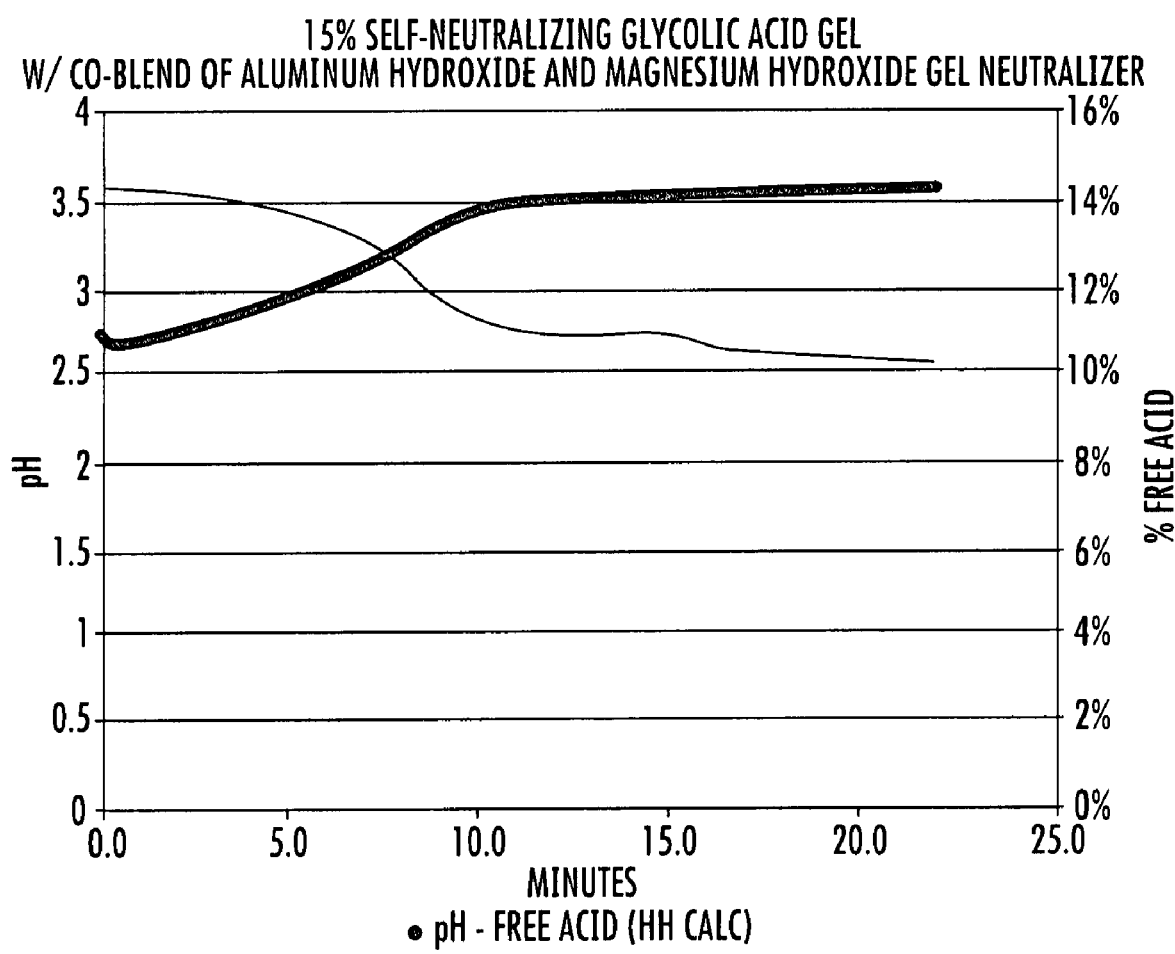
FIG. 5 is a graph similar to FIG. 1, showing a 15% self-neutralizing alpha hydroxy acid concentration of the invention prepared from a co-blended aluminum hydroxide and magnesium hydroxide gel neutralizer and a 30% by weight alpha hydroxy acid.

FIG. 5 shows a graph of the pH of the system of Example 5 as neutralization occurs over time. The free acid, in percent by weight of the mixed solution starting from a 15% by weight glycolic acid solution, is also shown correlated with pH. The free acid equilibrium concentration is calculated from the Henderson-Hasselbalch equation based on the pH of the system over time. As illustrated in FIG. 5, the pH of the system increases continually over time from about 2.7 to about 3.5 or 3.6. The percent free acid continuously reduces, from about 19% to 11% within about 20 minutes. Example 5 shows that a co-blend of aluminum hydroxide and magnesium hydroxide can be used as a time-release neutralizer for glycolic acid. The acid neutralizing power of the co-blend is not as high as for the magaldrate neutralizer used in Examples 1 through 4. More neutralizer would be required to bring the final pH to a pH compatible with all skin types.

Example 6

| Acid Gel Component 30% Glycolic Acid Gel | Grams | Percent | Effective Acid |
|---|---|---|---|
| D.I. Water | 46.14 | 46.1% | |
| Cellosize PCG-10 | 0.8 | 0.8% | |
| Ticaxan (Salt resistant) | 0.2 | 0.2% | |

-continued

| Acid Gel Component 30% Glycolic Acid Gel | Grams | Percent | Effective Acid |
|---|---|---|---|
| Propylene glycol | 10 | 10.0% | |
| Glycolic Acid, 70% | 42.86 | 42.9% | 30.0% |
| | 100 | 100% | |

| Neutralizer Gel Component Aluminum Hydroxide | |
|---|---|
| Aluminum Hydroxide | 12% |
| Carbonate | Present |

The same 30% glycolic acid gel is used in Example 6 as was used in Examples 1 and 5. However, instead of using the 20% magaldrate neutralizer of Example 1 or the co-blend neutralizer of Example 5, Example 6 blends with the acid component aluminum hydroxide present in similar amounts as the aluminum hydroxide in the magaldrate formulation and in the co-precipitated product. Carbonate is present in small amounts as noted on the above table.

Ten grams of the acid gel and 10 grams of the neutralizer aluminum hydroxide were mixed together in a 50 ml beaker and the pH of the gel mixture was measured over time using a pH data acquisition system. Free acid was determined to be a nominal 15% by weight, the acid concentration having been reduced by half by mixing the acid gel with the neutralizer gel in a 50/50 weight ratio.

Figure 6:
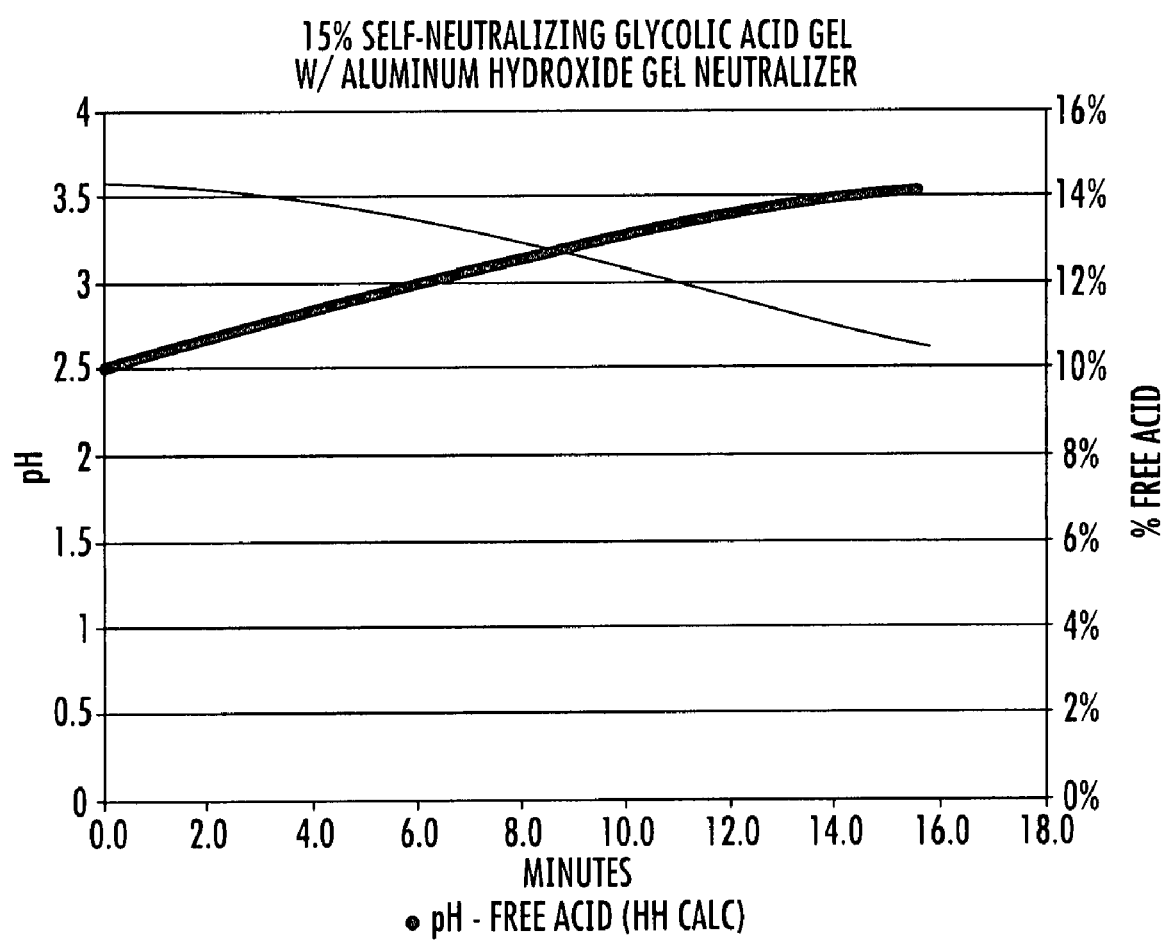
FIG. 6 is a graph similar to FIG. 1, showing a 15% self-neutralizing alpha hydroxy acid concentration of the invention prepared from a 30% by weight acid component and an aluminum hydroxide gel neutralizer.

FIG. 6 shows a graph of the pH of the system of Example 6 as neutralization occurs over time. The free acid, in percent by weight of the mixed solution starting from a 15% by weight glycolic acid solution, is also shown correlated with pH. The free acid equilibrium concentration is calculated from the Henderson-Hasselbalch equation based on the pH of the system over time. As illustrated in FIG. 6, the pH of the system increases continually over time from about 2.6 to about 3.5. The percent free acid continually reduces, from about 14% to 10% within about 16 minutes. Example 6 shows that aluminum hydroxide can be used as a time-release neutralizer for glycolic acid. The acid neutralizing power of the aluminum hydroxide is not as high as for the magaldrate neutralizer used in Examples 1 through 4. More neutralizer would be required to bring the final pH to a pH compatible with all skin types.

Figure 7:
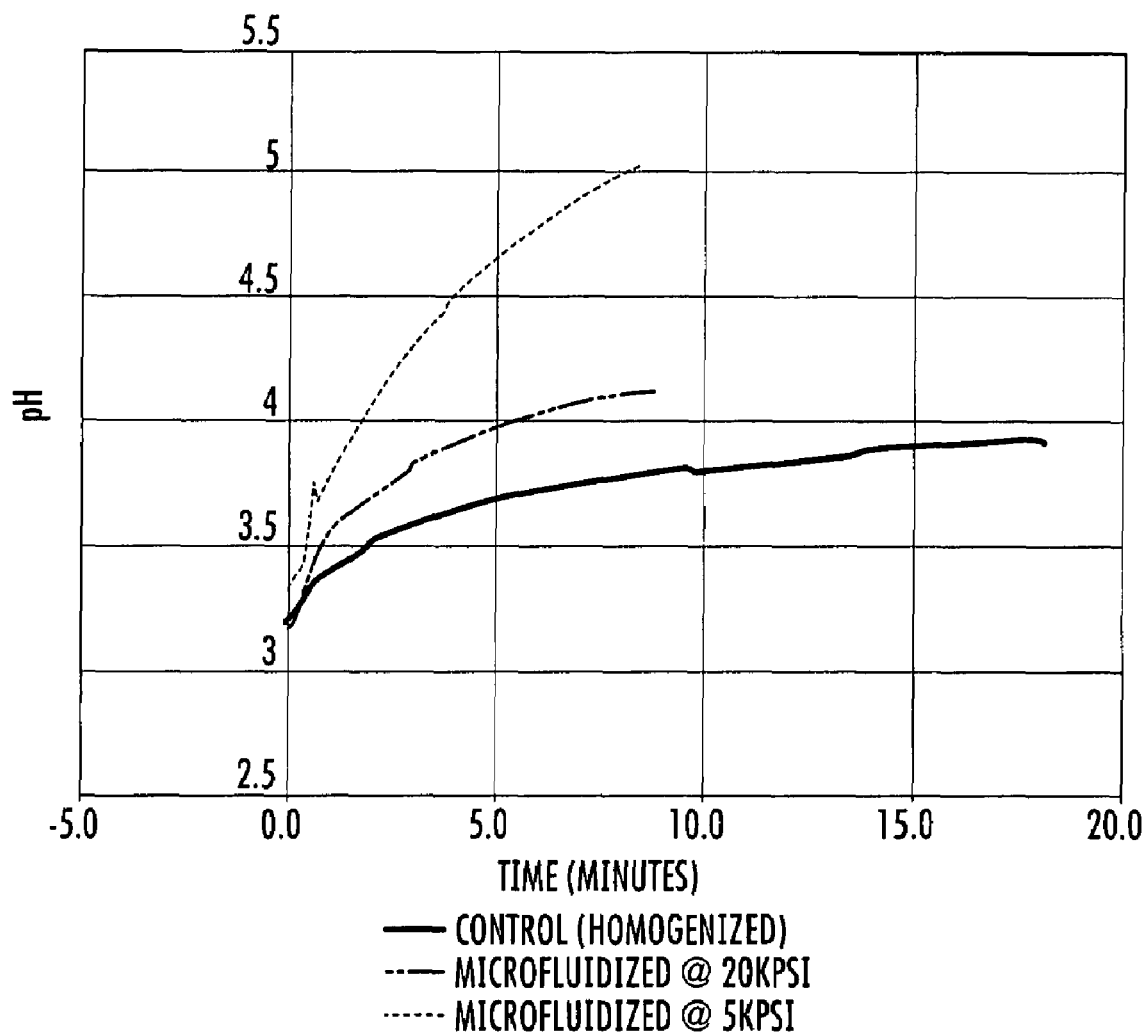
FIG. 7 is a graphical representation of the impact of fluidization conditions on self-neutralization performance for a fluidized 20% magaldrate gel mixed with a 40% glycolic acid gel.

FIG. 7 illustrates the impact of microfluidization on the neutralization performance of the magaldrate in the formulations of the invention. Microfluidization is a process of applying mixing forces at high shear to a suspension to increase the stability of the suspension. Microfluidization equipment of the type used for these experiments is available from Microfluidics, Inc, which is located in Newton, Mass.

Magaldrate compositions are susceptible to settling out and separation over time. For the two-component system of the invention, it is contemplated that the acid and magaldrate components may be prepackaged for single use dispensing and it would be desirable to increase the shelf life of the magaldrate composition to avoid settling out of the magaldrate components.

In each of the above examples, the magaldrate was mixed with standard mixing equipment to homogenize the magaldrate, and excellent results were obtained. However, microfluidizing the magaldrate to increase potential shelf life of the prepackaged two-component, single-use, dermatologic peel of the invention resulted in the benefit of increasing neutralization performance, as is demonstrated in FIG. 7. Both systems in which the magaldrate component is microfluidized performed better than with magaldrate that is homogenized on standard mixing equipment.

As shown in FIG. 7, a homogenized control was prepared from a 20% magaldrate gel fluidized in standard mixing equipment. The fluidized magaldrate was then mixed in accordance with the invention with 40% glycolic acid gel. Neutralization performance of the control was compared to two formulations of the same concentration of 20% magaldrate gel mixed with 40% glycolic acid gel where the magaldrate had been subjected to microfluidization at two different shear rates. In one case, the magaldrate was subjected to microfluidization at a pressure of about 5,000 pounds per square inch ("psi") prior to mixing with the acid, and in another case was microfluidized at about 20,000 psi. The pH of the resulting mixture of acid and fluidized neutralizer gels shows the neutralization performance of the mixture.

Magaldrate gels microfluidized at about 5,000 psi mixed easily with the glycolic acid gels and provided superior neutralization performance when compared to magaldrate gels mixed with standard homogenizing equipment at low shear. Magaldrate gels microfluidized at about 20,000 psi had viscosities and particle sizes that inhibited ability to mix the magaldrate gel with the acid gel and provided somewhat inconsistent neutralization performance. When mixed sufficiently, the acid neutralization was better than for the control gel in which the magaldrate was fluidized with standard homogenizing equipment. However, if not properly mixed, then the system performance was rated below that for standard homogenizing equipment Microfluidization can be accomplished at pressures of from about 2000 psi up to about 35,000 psi. As noted above, the benefits of microfluidization in the practice of the invention can be achieved over a wide range of pressures and it is believed that prepackaged two-component systems could be prepared with significantly extended shelf lives using the full range of microfluidization pressures. For ease of mixing of the components and the most effective neutralization performance, it is believed that the lower range of microfluidization pressures, of from about 2000 to 7500 psi is desirable. Above about 7500 psi, then more mixing may be useful to maximize neutralization performance, though with adequate mixing, performance should still exceed that of systems in which magaldrate is homogenized on standard mixing equipment.

Two clinical studies were performed that demonstrated that the self-neutralizing glycolic acid peels of the invention did not elicit irritation or sensitization responses with acid phase concentrations up to 50% by weight. In each study the acid was mixed with a 10% to 20% magaldrate solution, by weight. The objective of this study was to evaluate different formulations of the self-neutralizing acid peel for their potential to cause irritation after a single 24-hour patch application. The primary irritation patch test is a standard test for evaluating cosmetic products, and the 24-hour patch application has the added benefit of demonstrating the effect of leaving the product on without neutralizing or rising it off.

In the first study, four acid formulations were used as noted in Table 2 below:

TABLE 2

| Code | Description |
|---|---|
| A | 30% Glycolic Acid Gel with 20% Magaldrate Neutralizer Gel (50/50 by weight); |
| B | 30% AHCare G-60 Gel with 20% Magaldrate Neutralizer Gel (50/50 by weight); |
| C | Control: 30% Glycolic Acid Gel, unbuffered, pH ~ 1.9; |
| D | Control: 10% Glycolic Acid Gel, buffered to a pH >= 3.5 |

The 30% glycolic acid unbuffered control C was formulated to compare the response to a standard glycolic acid treatment that was not manually buffered with the response to a self-neutralizing acid peel treatment of the invention. Control D was used to compare the test formulations to the guidelines established by the Cosmetic Ingredient Review (CIR) for consumer glycolic acid products used in the home. The CIR guidelines for AHAs are published in the first supplement to volume 17 of the 1998 International Journal of Toxicology at pages 1 through 3.

Eighteen subjects, male and female, were selected to participate in the study. The patches were worn for 24 hours and then removed. The test sites were visually inspected and the results are presented in Table 3, below, with a key to the evaluation codes following.

TABLE 3

| | Treatment | | | |
|---|---|---|---|---|
| Subject | A. Self-Neutralizing 30% GA | B. Self-Neutralizing 30% AHCare | C. Unbuffered 30% GA | D. 10% GA @ pH >= 3.5 |
| 1 | 0 | 0 | 1Vy | 0 |
| 2 | 0 | 0 | 1P, 1g | 0 |
| 3 | 0 | 0 | 2SV, 2PS | 0 |
| 4 | 0 | 0 | 2B, 2gy | 1 |
| 5 | 0 | 0 | 0gy | 0 |
| 6 | 0 | 0 | 2S, 3gyS | 0 |
| 7 | 0 | 0 | 3, 31 | 0 |
| 8 | 0 | 0 | 3PgS, 2gyS | 0 |
| 9 | 0 | 0 | 3B, 3yg | 0 |
| 10 | 0 | 0 | 1y, 1y | 0 |
| 11 | 0 | 0 | 2SV, 3gy | 0 |
| 12 | 0 | 0 | 2B, 3g | 1 |
| 13 | 0 | 0 | 1, 2VgyS | 0 |
| 14 | 0 | 0 | 2V, 2gy | 0 |
| 15 | 0 | 0 | 2PygS | N/A |
| 16 | 0 | 0 | 3, 3g | 0 |
| 17 | 0 | 0 | 1Syg, 1yS | 0 |

Table 3 shows that the self-neutralizing formulations had no measurable irritation response ("0") while the unbuffered 30% glycolic acid had significant response in all 18 subjects. In two subjects, 4 and 12, the unbuffered control formulated to the CIR guidelines, Control C, showed a slight response.

The primary measurement taken was by visual evaluation of irritation according to the following protocol: All sites were scored once at 30 minutes (±5 minutes) after patch application and again approximately 24 (±1) hours after patch removal, which is approximately 48 hours after the application of the final patch. A 100 watt incandescent blue bulb lamp provided a consistent artificial light source to illuminate the patch areas. All skin reactions were recorded. A single entry in the Table 3 columns indicates that the same response was recorded at 30 minutes after patch applications and again 24 hours after the patch was removed. Two entries separated by a comma indicate that different responses were obtained. The scorer was blinded as to treatment assignments and any previous scores. All reasonable attempts were made to ensure that the same individual scored reactions to the patches during the course of the study. Scores for erythema, edema, papules and vesicles were judged to be present if they involved 25% or more of the patch site. Identifiable reaction(s) encompassing less than 25% of the patch site area were documented on the scoring sheet as no visible reaction.

The following Table 4 presents definitions of the scoring codes recorded in Table 3:

TABLE 4

| Code | Description |
|---|---|
| 0 | No visible reaction and/or erythema |
| 1 | Mild reaction - macular erythema (faint, but definite pink) |
| 2 | Moderate reaction - macular erythema (definite redness, similar to a sunburn) |
| 3 | Strong to severe reaction - macular erythema (very intense redness) |
| E | Edema - swelling, spongy feeling when palpated |
| P | Papules - red, solid, pinpoint elevations, granular feeling |
| V | Vesicles - small elevation containing serous fluid (blister-like), diameter 5 mm or less |
| B | Bulla reaction - fluid-filled lesion greater than 0.5 cm in diameter |
| S | Spreading - evidence of the reaction beyond the test site |
| W | Weeping - result of a vesicular or bulla reaction - serous exudate - clear fluid oozing or covering patch site |
| I | Induration - solid, elevated, hardened, thickening skin reaction |
| L | Test patch worn less than 23 hours |
| g | Glazing |
| Y | Peeling |
| c | Scab, dried film of serous exudates of vesicular or bulla reaction |
| d | Hyperpigmentation (reddish-brown discoloration of test site) |
| h | Hypopigmentation (loss of visible pigmentation at test site) |
| f | Fissuring - grooves in the superficial layers of the skin |

A second study was designed to test the primary irritation response to increased strength formulations and reduced amounts of neutralizer using the following examples set forth in Table 5:

TABLE 5

| Code | Description |
|---|---|
| A | 30% Glycolic Acid Gel with 20% Magaldrate Neutralizer Gel (50/50 by weight); |
| B | 30% AHCare G-60 Gel with 20% Magaldrate Neutralizer Gel (50/50 by weight); |
| C | 40% Glycolic Acid Gel with 20% Magaldrate Neutralizer Gel (50/50 by weight); |
| D | 50% AHCare G-60 Gel with 20% Magaldrate Neutralizer Gel (50/50 by weight); |
| E | 50% Glycolic Acid Gel with 20% Magaldrate Neutralizer Gel (50/50 by weight); |
| F | 30% Glycolic Acid Gel with 10% Magaldrate Neutralizer Gel (50/50 by weight); |
| G | 30% AHCare G-60 Gel with 10% Magaldrate Neutralizer Gel (50/50 by weight); |

Seventeen subjects, male and female participated in the second test. The patches were worn for 24 hours and then removed. Overall, under the conditions of the study, all of the formulations were essentially non-irritating. A strong to severe reaction elicited during the primary irritation phase of the test by one subject was inconclusive and the origin of the reactions was indeterminate. The reactions did not indicate a sensitization reaction. The subject, however, did have significant reactions to the adhesives.

It should be recognized that the formulations of the invention can be tailored to specific skin types, including different skin types that need different levels of bioactivity. The initial pH, free acid strength, and the time can all be controlled to create formulations that are marketed to specific population segments. Manual neutralization of large surface areas is difficult to manage and it is believed that the invention may be useful in full-body treatments given its self-neutralizing capacity. Medical peels could be formulated that are particularly aggressive and include analgesics in the formulation, if desired.

What is claimed is:

1. A two-component system for applying a self-neutralizing dermatologic peel composition, said two-component system comprising a first container of at least one alpha hydroxy acid component and a second container of neutralizer component, said system further comprising a mixer for mixing the acid and neutralizer components to make said self-neutralizing dermatologic peel composition and establish an initial free acid concentration for said composition of above 10% by weight at a pH of less than 3.5, said free acid concentration continually reducing over time upon mixing of said acid component and said neutralizer component, and a dispenser for dispensing said composition onto the skin, whereupon the free acid concentration reduces continually over time from said initial concentration at a rate sufficient to substantially stop exfoliation and to increase the pH of the composition to a substantially skin-compatible pH in said predetermined treatment time.

2. The system of claim 1 wherein said first and second containers are piston-actuated dispensing tubes fitted with pistons, said mixer is a static mixing head in a chamber in flow communication with each of said first and second tubes and into which said tubes dispense their contents, and said dispenser is a narrow portion of said chamber distal to said first and second tubes.

3. The system of claim 1 wherein said free acid concentration is the bioavailable acid concentration.

4. The system of claim 1 wherein said alpha hydroxy acid component comprises glycolic acid.

5. The system of claim 1 wherein said neutralizer component comprises magaldrate.

6. The system of claim 1 wherein said neutralizer component comprises at least one insoluble inorganic metal hydroxide.

7. The system of claim 1 wherein said alpha hydroxy acid component contains acid in a concentration of from about 15% to about 70% by weight prior to mixing with said neutralizer component.

8. The composition of claim 7 wherein said acid component comprises in addition to the acid a neutralizer component in a shelf-stable formulation.

9. The composition of claim 1 wherein said neutralizer component is microfluidized.

10. The composition of claim 1 wherein said neutralizer component is microfluidized magaldrate.

11. A method for applying a dermatologic peel comprising first mixing an alpha hydroxy acid in a concentration sufficient to establish a bioavailable acid concentration efficacious for a dermatologic peel with a neutralizer for continually reducing the bioavailable acid concentration while applied to the skin over a predetermined time period, and then applying the peel to the skin, whereby the pH of the applied peel reaches approximately a skin-compatible pH in said predetermined time period.

12. The method of claim 11 wherein the peel has an initial pH of about 2.5 to 3.5 at an acid concentration in the mixed acid and neutralizer of from 15% to 35% and reaches a pH of at least about 4.25 within about 3 to 5 minutes.

13. The method of claim 11 wherein said acid is glycolic acid and said neutralizer comprises aluminum hydroxide.

14. The method of claim 11 wherein said neutralizer comprises magaldrate.

15. The method of claim 11 wherein said neutralizer comprises microfluidized magaldrate thus combining efficacy and safety.

* * * * *